United States Patent
Kang

(10) Patent No.: US 11,645,931 B2
(45) Date of Patent: *May 9, 2023

(54) TRAINING METHOD, PROGRAM AND COMPUTING DEVICE FOR AMELIORATING VISUAL FIELD DEFECT

(71) Applicant: NUNAPS INC., Seoul (KR)

(72) Inventor: Dong Wha Kang, Seoul (KR)

(73) Assignee: NUNAPS INC., Seoul (KR)

( * ) Notice: Subject to any disclaimer, the term of this patent is extended or adjusted under 35 U.S.C. 154(b) by 0 days.

This patent is subject to a terminal disclaimer.

(21) Appl. No.: 17/679,881

(22) Filed: Feb. 24, 2022

(65) Prior Publication Data

US 2022/0180761 A1 Jun. 9, 2022

Related U.S. Application Data

(63) Continuation of application No. 17/076,249, filed on Oct. 21, 2020, now Pat. No. 11,295,627, which is a (Continued)

(30) Foreign Application Priority Data

Nov. 29, 2018 (KR) .......................... 10-2018-0151354
Nov. 28, 2019 (KR) .......................... 10-2019-0155788

(51) Int. Cl.
*G09B 5/02* (2006.01)
*A61B 3/024* (2006.01)
(Continued)

(52) U.S. Cl.
CPC .............. *G09B 5/02* (2013.01); *A61B 3/024* (2013.01); *A61B 3/066* (2013.01); *G06F 1/163* (2013.01)

(58) Field of Classification Search
CPC ........... G09B 5/02; A61B 3/024; A61B 3/066; A61B 3/113; A61H 5/00
See application file for complete search history.

(56) References Cited

U.S. PATENT DOCUMENTS 11,295,627 B2 * 4/2022 Kang .................. G06F 3/04842

FOREIGN PATENT DOCUMENTS

JP 2005-516679 A 6/2005
KR 10-2006-9013880 A 2/2006
(Continued)

OTHER PUBLICATIONS

International Search Report issued in PCT/KR2019/016734; dated Apr. 17, 2020.

*Primary Examiner* — Robert J Utama
*Assistant Examiner* — Correll T French
(74) *Attorney, Agent, or Firm* — Studebaker & Brackett PC

(57) ABSTRACT

Disclosed are training method, program and computing device to ameliorate visual field defect. The method includes presenting, by a computer, a virtual first object on a screen, wherein the first object is presented in an approaching manner toward the subject from a first position to a second position, when a position of the first object reaches the second position, the dividing, by the computer, of the first object into objects and presenting the divided objects on the screen or removing, by the computer, the first object from the screen, when the first object is divided or removed, presenting, by the computer, a virtual second object and a virtual third object on the screen, and receiving, by the computer, an identification input about the second object and the third object from a response input device of the subject.

20 Claims, 13 Drawing Sheets

Related U.S. Application Data continuation of application No. PCT/KR2019/016734, filed on Nov. 29, 2019.

(51) Int. Cl.
    *A61B 3/06*     (2006.01)
    *G06F 1/16*     (2006.01)

(56) References Cited

FOREIGN PATENT DOCUMENTS

| | | |
|---|---|---|
| KR | 10-0876085 B1 | 12/2008 |
| KR | 10-2012-0062728 A | 6/2012 |
| KR | 10-2012-0139670 A | 12/2012 |
| WO | 2004-066900 A1 | 8/2004 |

\* cited by examiner ized as permanent defect, such that there is no rehabilitation attempt of the visual field defect. The subject having damage in a brain visual cortex due to the stroke characteristically exhibits a hemianopia on an opposite side to a lesion side. For example, a subject having a stroke in a left visual cortex exhibits a hemianopia on a right side. In this connection, the subject cannot recognize objects or movements thereof on a right visual field when looking straight ahead with both eyes open.

TRAINING METHOD, PROGRAM AND COMPUTING DEVICE FOR AMELIORATING VISUAL FIELD DEFECT

CROSS-REFERENCE TO RELATED APPLICATIONS

The present application is a continuation of U.S. patent application Ser. No. 17/076,249, filed on Oct. 21, 2020, which is a continuation of International Patent Application No. PCT/KR2019/016734, filed on Nov. 29, 2019, which is based upon and claims the benefit of priority to Korean Patent Application Nos. 10-2018-0151354 filed on Nov. 29, 2018 and 10-2019-0155788 filed on Nov. 28, 2019. The disclosures of the above-listed applications are hereby incorporated by reference herein in their entirety.

BACKGROUND

Embodiments of the inventive concept described herein relate to a training method, a program, and a computing device for ameliorating a visual field defect.

In general, stroke is the number one cause of disability in Korea as a single disease. Among brain function damage caused by the stroke, visual field defect is a major disorder that appears at a high percentage of 20 to 30% of the total number of subjects. The visual field defect is generally accepted as permanent defect, such that there is no rehabilitation attempt of the visual field defect. The subject having damage in a brain visual cortex due to the stroke characteristically exhibits a hemianopia on an opposite side to a lesion side. For example, a subject having a stroke in a left visual cortex exhibits a hemianopia on a right side. In this connection, the subject cannot recognize objects or movements thereof on a right visual field when looking straight ahead with both eyes open.

However, among subjects having visual field defect caused by strokes occurring in the visual cortex, some subjects may notice a movement or a form in an invisible visual field. In this case, when an X or O character is placed in the invisible visual field of the subjects, and the subjects are asked to answer the character, the subject may answer that the character is invisible, but may correctly answer the character at a probability above a chance level, and may even respond appropriately to visual stimulus. The subject cannot visually perceive the stimulus, but a brain thereof is aware of the movement or the form. This phenomenon was discovered by Lawrence Weiskrantz in the 1970s, and then is called blindsight. The blindsight refers to a phenomenon that an object is noticed by a subject even though the object is invisible thereto. The existence of the above-described blindsight phenomenon suggests that visual information inputted through a retina may be processed by a site other than the visual cortex.

Accordingly, there is a need for a visual perception training method and device that allows a subject to perform visual perception training by applying repetitive visual perception stimulus thereto, thereby to improve a visual perception function thereof.

Prior Art literature: Patent Literature: Korean Patent No. 10-0876085 (2008 Dec. 29).

SUMMARY

In a conventional method for performing visual perception training for a subject with the visual field defect, the subject has to be positioned such that a distance and a height between a display and an eye position of the subject meet a predetermined distance and a predetermined height, respectively. Thus, this is inconvenient for the subject.

Further, the distance from the subject's eye position to the display is predetermined. Thus, only stimulus at a specific depth may be applied to the subject, but stimulus varying according to various depths may not be applied thereto.

Therefore, embodiments of the inventive concept provide training method, program and computing device for ameliorating visual field defect in which concentration of the subject is induced and stimulus varying according to various depths is applied to the subject.

Further, embodiments of the inventive concept provide training method, program and computing device for ameliorating visual field defect in which stimulus is continuously applied to a non-central visual field while a subject fixes a gaze direction to a central visual field while an object is moving from a position far away from the subject to a position close to the subject and in the central visual field.

Further, embodiments of the inventive concept provide training method, program and computing device for ameliorating visual field defect in which training for ameliorating visual field defect is embodied in a game manner.

Purposes to be solved by the inventive concept are not limited to the purposes as mentioned above. Other purposes not mentioned will be clearly understood by those skilled in the art from following descriptions.

According to an exemplary embodiment, a method for training a subject to ameliorate visual field defect of the subject includes presenting, by a computer, a virtual first object on a screen, wherein the first object is presented in an approaching manner toward the subject from a first position to a second position, when a position of the first object reaches the second position, the dividing, by the computer, of the first object into objects and presenting the divided objects on the screen or removing, by the computer, the first object from the screen, when the first object is divided or removed, presenting, by the computer, a virtual second object and a virtual third object on the screen, and receiving, by the computer, an identification input about the second object and the third object from a response input device of the subject, wherein at the first position, at least one of a position, a size, and a shape of the first object starts to change, wherein at the second position, the change of the at least one of the position, the size, and the shape of the first object is completed, wherein the first position and the second position are present in a central visual field of the subject, Each of the second object and the third object may be positioned in at least one of the central visual field of the subject, a normal region of a subject visual field, or a defect region of the subject visual field.

The first object may be presented in the central visual field of the subject, wherein an angle of the first object relative to the subject, a distance of the first object from the subject, and a speed at which the first object moves toward the subject may vary on a subject basis.

The presenting, by the computer, of the virtual second object and the virtual third object on the screen may include presenting the second object and the third object as a first combination therebetween, wherein the first combination is configured such that one of the second object and the third object is positioned in the normal region of the subject visual field, while the other thereof is positioned in the defect region of the subject visual field.

The presenting, by the computer, of the virtual second object and the virtual third object on the screen may include presenting the second object and the third object as the first combination and a second combination therebetween at a predetermined ratio of the first and second combinations, wherein the second combination is configured such that the second object and the third object are positioned in the normal region of the subject visual field.

The presenting, by the computer, of the virtual second object and the virtual third object on the screen may include presenting the second object and the third object as a third combination, wherein the third combination is configured such that one of the second object and the third object is positioned at the central visual field of the subject, while the other thereof is positioned in the defect region of the subject visual field.

The dividing, by the computer, of the first object into the objects and presenting the divided objects on the screen or removing, by the computer, the first object from the screen may include, when the computer divides the first object into the objects and presents the divided objects on the screen, dividing the first object at the second position into a first divided object and a second divided object and presenting the first divided object and the second divided object, wherein a depth at which each of the first divided object and the second divided object during the division of the first object thereinto is adjusted, wherein the presenting, by the computer, of the virtual second object and the virtual third object on the screen includes presenting the first divided object and the second divided object into which the first object is divided, and then replacing the first divided object and the second divided object with the virtual second object and the virtual third object, respectively and presenting the virtual second object and the virtual third object in a predetermined region.

The dividing, by the computer, of the first object into the objects and presenting the divided objects on the screen or removing, by the computer, the first object from the screen may include, when the computer removes the first object from the screen, removing the first object from the screen in a scattered manner from the second position, removing the first object from the screen in a spreading manner from the second position, or removing the first object from the screen in a scattered manner or in a spreading manner from the second position while a depth at which the first object as being scattered or spread is present is adjusted.

The screen may be a screen on a head mounted display, wherein the presenting, by the computer, of the virtual first object on the screen may include displacing a stimulus recognized position of the first object, and when recognition of the first object at the displaced stimulus recognized position by the subject is detected by the head mounted display, presenting the first object such that the first object moves in an approaching manner from the first position to the second position on the screen.

The presenting, by the computer, of the virtual first object on the screen may include presenting the first object such that a color of the first object at the first position is different from a color of the first object at the second position.

The presenting, by the computer, of the virtual second object and the virtual third object on the screen may include randomly presenting the second object and the third object to have a horizontal pattern and/or a vertical pattern, wherein the patterns of the second object and the third object are the same as or different from each other.

The presenting, by the computer, of the virtual second object and the virtual third object on the screen may include randomly presenting the second object and the third object such that the second object and the third object are rotating, wherein the rotation directions of the second object and the third object are the same as or different from each other.

The presenting, by the computer, of the virtual second object and the virtual third object on the screen may include randomly presenting the second object and the third object such that depths on the screen at which the second object and the third object are presented respectively are the same as or different from each other, wherein the depth at which the second object or the third object is presented corresponds to a distance of the second object or the third object from the subject's eye position.

The presenting, by the computer, of the virtual second object and the virtual third object on the screen may include varying at least one of a size, a position, an exposure time duration, or a contrast of each of the second object and the third object based on a predetermined setting.

The second object and the third object may be positioned in a diagonal direction with respect to the subject's central visual field, wherein the presenting, by the computer, of the virtual second object and the virtual third object on the screen may include presenting the second object and the third object within a visual field of the subject, wherein an angle between the visual field central and each of positions at which the second object and the third object are presented respectively is adjusted based on a subject's manipulation.

According to an exemplary embodiment, a visual field defect-ameliorating training program stored in a storage medium may execute the method as defined above when the program is combined with a computer as hardware.

According to an exemplary embodiment, a computing device for performing visual field defect-ameliorating training includes a controller, and an input receiver, wherein the controller presents a virtual first object on a screen, wherein the first object is presented in an approaching manner toward the subject from a first position to a second position, wherein when a position of the first object reaches the second position, the computer divides the first object into objects and presents the divided objects on the screen or remove the first object from the screen, wherein when the first object is divided or removed, the computer presents a virtual second object and a virtual third object on the screen, wherein the input receiver receives an identification input about the second object and the third object from a response input device of the subject, wherein at the first position, at least one of a position, a size, and a shape of the first object starts to change, wherein at the second position, the change of the at least one of the position, the size, and the shape of the first object is completed, wherein the first position and the second position are present in a central visual field of the subject, wherein each of the second object and the third object is positioned in at least one of the central visual field of the subject, a normal region of a subject visual field, or a defect region of the subject visual field.

BRIEF DESCRIPTION OF THE FIGURES

The above and other objects and features will become apparent from the following description with reference to the following figures, wherein like reference numerals refer to like parts throughout the various figures unless otherwise specified, and wherein.

DETAILED DESCRIPTION

Figure 1:
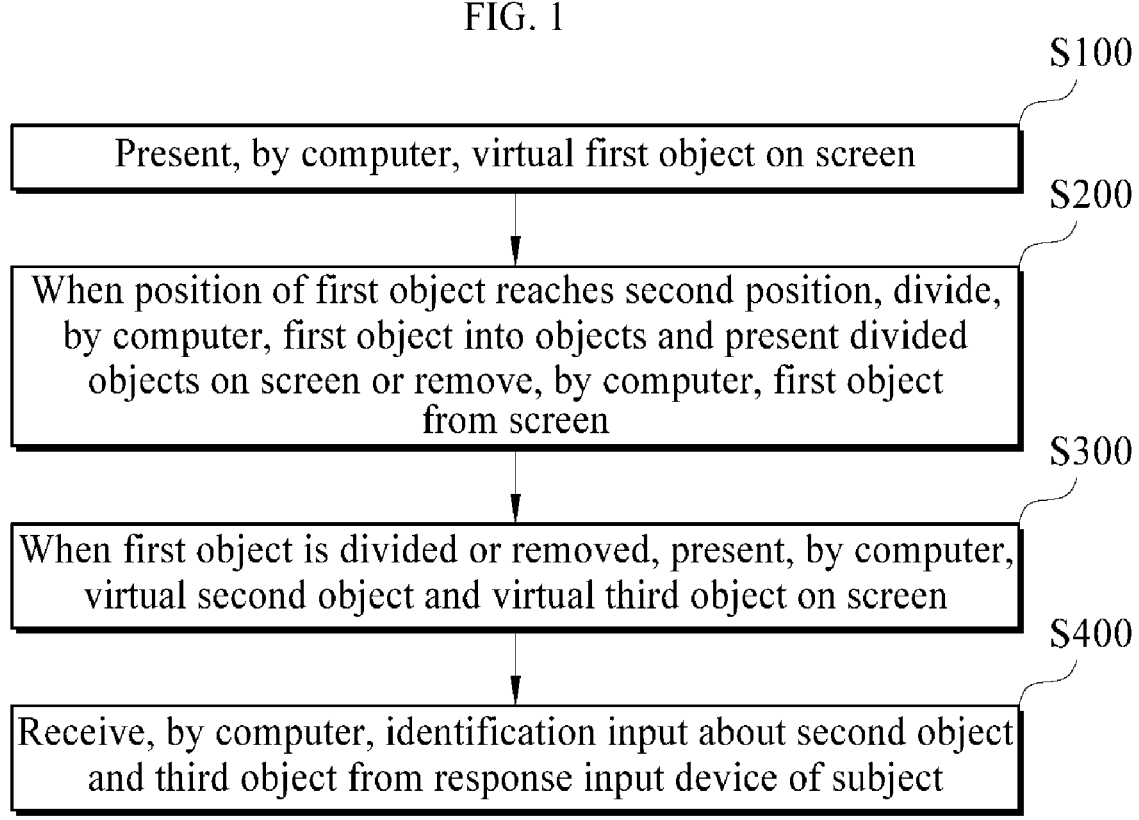
FIG. 1 is a diagram for describing a training method for ameliorating visual field defect according to an embodiment of the inventive concept.

Advantages and features of the inventive concept, and a method of achieving them will become apparent with reference to embodiments described below in detail together with the accompanying drawings. However, the inventive concept is not limited to the embodiments disclosed below, but may be implemented in various different forms. The present embodiments are provided to merely complete the disclosure of the inventive concept, and to merely fully inform those skilled in the art of the inventive concept of the scope of the inventive concept. The inventive concept is only defined by the scope of the claims.

The terminology used herein is for the purpose of describing the embodiments only and is not intended to limit the inventive concept. As used herein, the singular forms "a" and "an" are intended to include the plural forms as well, unless the context clearly indicates otherwise. It will be further understood that the terms "comprises", "comprising", "includes", and "including" when used in this specification, specify the presence of the stated features, integers, operations, elements, and/or components, but do not preclude the presence or addition of one or greater other features, integers, operations, elements, components, and/or portions thereof. Like reference numerals refer to like elements throughout the disclosure. As used herein, the term "and/or" includes any and all combinations of one or more of the associated listed items. Although terms "first", "second", etc. are used to describe various components, it goes without saying that the components are not limited by these terms. These terms are only used to distinguish one component from another component. Therefore, it goes without saying that a first component as mentioned below may be a second component within a technical idea of the inventive concept.

Unless otherwise defined, all terms including technical and scientific terms used herein have the same meaning as commonly understood by one of ordinary skill in the art to which this inventive concept belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

Spatially relative terms, such as "beneath," "below," "lower," "under," "above," "upper," and the like, may be used herein for ease of explanation to describe one element or feature's relationship to another element or feature as illustrated in the figures. It will be understood that the spatially relative terms are intended to encompass different orientations of the device in use or in operation, in addition to the orientation depicted in the figures. For example, when the device in the figures is turned over, elements described as "below" or "beneath" or "under" other elements or features would then be oriented "above" the other elements or features. Thus, the example terms "below" and "under" may encompass both an orientation of above and below. The device may be otherwise oriented for example, rotated 90 degrees or at other orientations, and the spatially relative descriptors used herein should be interpreted accordingly.

The inventive concept may aim to treat the visual field defect by inducing brain plasticity, and may be applied as a digital therapeutic agent using therapeutic effect of the visual field defect (for example, visual field defect due to the visual cortex caused by the stroke) via inducing the brain plasticity.

Generally, surgery, procedure, or medicine may be prescribed to treat a patient. In this connection, the digital therapeutic agent may mean treating a patient using digital healthcare as a medicine. The digital therapeutic agent uses software such as applications, games, VR, chatbots, artificial intelligence, etc. without hardware, and may be used as a therapeutic agent only using the software. The software embedded in a medical device as hardware may play a role as the treatment agent.

As used herein, 'the computer' includes all of a variety of devices capable of performing computational processing. For example, the computer may include not only a desktop PC, and a notebook, but also a smart phone, a tablet PC, a cellular phone, a PCS phone (Personal Communication Service phone), a mobile terminal based on a synchronous/asynchronous IMT-2000 (International Mobile Telecommunication-2000), a palm personal computer (PC), a personal digital assistant (PDA), and the like. Further, the computer may include a head mounted display function. The head mounted display itself may be a computing device. The computer may be a computing device connected to the head mounted display in a wire or wireless manner, wherein the computing device may provide an image to the head mounted display. The computer may be a head mounted display computing device itself, which may generate and present an image. Further, the computer may be a server that receives information from a client. Hereinafter, as used herein, the computer may be expressed as a terminal or a client.

As used herein, the term 'head mounted display' means a device for presenting a visual field defect-ameliorating training image to the subject's eyes. The inventive concept is related to a training method for ameliorating the visual field defect, where the method is performed in two-dimension and three-dimension (virtual reality: VR). When the method is performed in the three-dimension, the 'head mounted display' is used for the method. The 'head mounted display' may be a device connected to the computer (e.g., a PC or a smartphone), or a device including a computing function.

As used herein, the term 'screen' to be presented to the subject may include a separate display screen in case of training execution in two-dimension, and a screen on the head mounted display worn by the subject in case of training execution in three-dimension.

As used herein, the term 'central visual field region' refers to a central region within a screen presented to the subject.

As used herein, the term 'non-central visual field region' refers to a remaining region in the screen excluding the central visual field region.

As used herein, the term 'a first object' serves as a fixation point for the visual field defect-ameliorating training, and acts as a stimulus that fixes a center of a visual field of the subject. The first object may be of a two-dimension form or a three-dimension form. Further, the first object may be divided or removed before appearance of a second object and a third object to be described later. Alternatively, the first object may be removed after the appearance of the second object and the third object. While the first object is removed, the first object may be divided into the second object and the third object which in turn are presented. A manner in which the first object is divided or removed will be described later.

As used herein, the terms 'a first divided object' and 'a second divided object' refer to objects which the first object is divided into. Each of the first divided object and the second divided object may have the same size and/or the same shape as those of the first object, and may have a different size and/or a different shape than those of the first object. Further, the 'first divided object' and the 'second divided object' may be changed to or replaced with 'a second object' and 'a third object' at a certain point in time.

As used herein, the terms 'a second object' and 'a third object' refer to stimulus (Gabor) applied to at least one of a central visual field, a visual field defect region, and a normal region. A specific stimulus applied region will be described in detail in following embodiments.

As used herein, the term 'a stimulus recognized position' refers to an initial position in which the first object is placed. The first object is placed at the stimulus recognized position such that the subject recognizes the first object as the stimulus in the central visual field.

Hereinafter, an embodiment of the inventive concept will be described in detail with reference to the accompanying drawings.

FIG. 1 is a diagram for describing a training method for ameliorating visual field defect according to an embodiment of the inventive concept.

Referring to FIG. 1, the training method for ameliorating the visual field defect according to an embodiment of the inventive concept includes step S100 in which the computer presents a virtual first object on the screen, step S200 in which when a position of the first object 10 reaches a second position, the computer divides and presents the first object 10 on the screen or removes the first object 10 therefrom, step S300 in which after the first object 10 is divided and presented or removed, the computer presents a virtual second object and a virtual third object on the screen, and step S400 in which the computer receives an identification input about the second object and the third object from the subject's response input device.

In step S100 in which the computer presents the virtual first object on the screen, the first object 10 is presented in an approaching manner from the first position to the second position on the screen.

As described above, the screen may include a separate display screen distant from a user in case of training execution in two-dimension, and a screen on the head mounted display worn by the subject in case of training execution in three-dimension.

The inventive concept may include both a visual field defect-ameliorating training method in two-dimension and a visual field defect-ameliorating training method in three-dimension.

The first position refer to a position at which at least one of a position, a size, and a shape of the first object 10 starts to change. The second position refers to a position at which change of at least one of a position, a size, and a shape of the first object 10 is completed.

In one embodiment, when the first object 10 moves in a virtual space, the position of the first object 10 is changed from the first position to the second position.

In another embodiment, when the size of the first object 10 is changed at a single position, the first position and the second position may be the same. In this case, as the size of the first object 10 on the screen changes (e.g., the first object 10 as presented has a small size and then has an increasingly larger size at a fixed position), the subject staring at the screen may recognize the size change as the first object 10 being moving.

Embodiments in which the first object 10 moves from the first position to the second position as described later may include a case where as the size of the first object 10 is changed without changing the position thereof, the subject may recognize the change of the size as the movement of the object. For example, the embodiment may include a case where the first object flies from the first position as a distant position from the subject to the second position as a near position to the subject, or case where the first position and the second position are the same and the first object 10 as presented has a small size and then has an increasingly larger size at the same position.

Further, the first position and the second position are positioned in the central visual field of the subject.

A manner in which the first object 10 moves in an approaching manner from the first position to the second position on the screen may include a manner in which the first object 10 flies from the first position as a distant position from the subject to the second position as a position closer to the subject on the screen and thus is presented as stimulus to the subject.

Further, the first object 10 may fly in the three-dimension and thus is presented as stimulus to the subject.

The first object 10 is presented in the central visual field region of the subject. An angle, a distance, and a speed at which the first object 10 is presented may vary depending on the subject individual and a state of the disease thereof. The angle, the distance and the speed are adjustable.

Presenting the first object 10 to the subject in the flying manner may allow fixing the visual field of the subject and inducing concentration thereof.

In the case of training execution in the three-dimension, in step S100 in which the computer presents the virtual first object 10 on the screen, the stimulus recognized position of the first object 10 is moved. When the recognition of the first object 10 at the moved stimulus recognized position is detected by the head mounted display, the first object 10 is presented to the subject such that the first object moves in an approaching manner from the first position to the second position on the screen.

Detailed descriptions of the case where the stimulus recognized position is moved thus the recognition of the first object 10 at the moved stimulus recognized position is detected by the head mounted display and then the first object 10 is presented to the subject such that the first object 10 move in the approaching manner will be described later in FIGS. 6A to 6C.

In step S100 in which the computer presents the first object on the screen, the first object 10 may be presented to having different colors at the first position and the second position.

In this way, changing the color of the approaching stimulus, that is, the approaching first object 10 toward the subject may allow the effect of fixing the central visual field to be improved.

In step S200 in which when a position of the first object 10 reaches the second position, the computer divides and presents the first object 10 on the screen or removes the first object 10 therefrom, a manner in which the first object 10 is divided and presented or removed may be implemented in various manners.

In one embodiment, the first object 10 may be removed in a scattered manner at the second position. In this connection, when the first object 10 is removed in a scattered manner, the first object 10 may be separated into a plurality of pieces at the second position and then the separated pieces are scattered up, down, left and right, and thus disappear.

In another embodiment, the first object 10 may be removed in a spreading manner at the second position. In this connection, when the first object 10 is removed in the spreading manner at the second position, the first object 10 at the second position gradually expands up, down, left and right, and at the same time gradually fades away. That is, the first object 10 gradually expands and thus gradually fades away in a proportional manner, and thus gradually disappears.

In another embodiment, the first object 10 may be divided into a first divided object 60 and a second divided object 70 in a diagonal direction at the second position which then may be presented to the subject.

In another embodiment, a presented depth of the first object 10 as scattered or spreading at the second position may be adjusted.

In another embodiment, when the first object 10 may be divided into the first divided object 60 and the second divided object 70 diagonally at the second position which then may be presented to the subject, a presented depth of each of the first divided object 60 and the second divided object 70 may be adjusted.

In step S300 in which after the first object 10 is divided and presented or removed, the computer presents the second object 20 and the third object 30 on the screen, the second object 20 and the third object 30 are presented to be positioned in at least one of the visual field center of the subject, the normal region of the subject visual field, and the defect region of the subject visual field.

In one embodiment, the second object 20 is presented to be positioned in the defect region of the subject visual field. The third object 30 is presented to be positioned in the visual field center of the subject, that is, a central region thereof. In another embodiment, the second object is presented to be positioned in the defect region of the subject visual field, and the third object 30 is presented to be positioned in the normal region of the subject visual field which is positioned diagonally to the second object 20 with respect to the central visual field.

In the above-described embodiment, when the first object 10 is divided into the first divided object 60 and the second divided object 70 at the second position which in turn are presented, step S300 of presenting the second object 20 and the third object 30 is performed as follows: after the first object 10 is divided into the first divided object 60 and the second divided object 70 which in turn are presented, the computer replaces the first divided object 60 and the second divided object 70 with a virtual second object 20 and a virtual third object 30, respectively in a predetermined region, which in turn are presented.

In this connection, one embodiment of a manner in which the first divided object 60 and the second divided object 70 are replaced with the virtual second object 20 and the virtual third object 30, respectively in the predetermined region, which in turn are presented may include a manner in which the first divided object 60 and the second divided object 70 are rotated and changed to the second object 20 and the third object 30, respectively.

In another embodiment, the first divided object 60 and the second divided object 70 disappear and, at the same time, are changed to the second object 20 and the third object 30, respectively.

In still another embodiment, the first divided object 60 and the second divided object 70 are blurred and changed to the second object 20 and the third object 30, respectively.

In yet still another embodiment, the first divided object 60 and the second divided object 70 are divided and changed to the second object 20 and the third object 30, respectively.

In yet still another embodiment, the first divided object 60 and the second divided object 70 become smaller and changed to the second object 20 and the third object 30, respectively.

The predetermined region refers to a region in which the second object 20 and the third object 30 should be placed for visual field defect-ameliorating training, or a surrounding region around the region in the second object 20 and the third object 30 should be placed for visual field defect-ameliorating training.

In one embodiment, when the first divided object 60 and the second divided object 70 reach the region in which the second object 20 and the third object 30 should be placed for visual field defect-ameliorating training, the second object 20 and the third object 30 may be presented to the subject.

In another embodiment, when the first divided object 60 and the second divided object 70 reach the surrounding region around the region in which the second object 20 and the third object 30 should be placed for visual field defect-ameliorating training, the second object 20 and the third object 30 may be presented in the region in which the second object 20 and the third object 30 should be placed for visual field defect-ameliorating training.

A depth at which the second object 20 and the third object 30 are presented may be adjusted. As the presented depth of each of the second object 20 and the third object 30 is adjusted, a depth thereof on the screen on which the stimulus for visual field defect-ameliorating training is presented may be adjusted. In one embodiment, the second object 20 and the third object 30 may have different presented depths in a virtual space. In another embodiment, the second object 20 and the third object 30 may be presented such that sizes thereof are different from each other such that it appears to the subject that the presented depths thereof are different from each other.

Therefore, performing the training while adjusting the presented depth on the screen of each of the second object 20 and the third object 30 as the stimulus for the training based on each subject and a defect state may allow the training for each state to be performed more effectively.

Further, the second object 20 and the third object 30 may be presented in various combinations, ratios, and the like.

In one embodiment, the second object 20 and the third object 30 are presented as a first combination therebetween, where one of the second object 20 and the third object 30 is positioned in the normal region of the subject visual field, while the other thereof is positioned in the defect region of the subject visual field. In this connection, the second object 20 and the third object 30 are presented in a diagonal direction to each other.

In another embodiment, the second object 20 and the third object 30 are presented as a second combination therebetween, where both the second object 20 and the third object 30 are positioned in the normal region of the subject visual field. In this connection, the second object 20 and the third object 30 are presented in a diagonal direction to each other. In still another embodiment, the second object 20 and the third object 30 are presented as a certain ratio of the first combination and the second combination. The certain ratio is a predetermined ratio.

In still another embodiment, the ratio of the first combination and the second combination between the second object 20 and the third object 30 as presented is 4:1.

Presenting the first combination as a stimulus combination in the visual field defect region, and the second combination as a stimulus combination in the normal region at the predetermined ratio may allow further increase in the training effect.

Further, when the ratio of the first combination and the second combination as presented is 4:1, the most effective training result is achieved.

In still another embodiment, the second object 20 and the third object 30 are presented as a third combination therebetween. In the third combination, one of the second object 20 and the third object 30 is positioned in the central visual field of the subject, while the other thereof is positioned in the defect region of the subject visual field.

When one of the second object 20 and the third object 30 is positioned in the central visual field of the subject, the visual field defect-ameliorating training is performed based on the other thereof positioned in the defect region of the subject visual field while the subject's gaze is not moved and is continuously fixed to the central visual field. Thus, the more effective training result is achieved The inventive concept is characterized in that the defect region is visible to the subject while the subject's gaze is not moved and is continuously fixed to the central visual field.

Among the above-described embodiments, both of the embodiment in which both of the objects are presented in a diagonal direction to each other and the embodiment in which one thereof is continuously presented in the central visual field while the other thereof is presented in the defect region may realize the above feature that the defect region is visible to the subject while the subject's gaze is not moved and is continuously fixed to the central visual field.

In step S300 of presenting the second object 20 and the third object 30, the second object 20 and the third object 30 may be presented as various stimulus types.

In one embodiment, the second object 20 and the third object 30 may be presented to have a horizontal pattern or a vertical pattern and may be presented to have the same or different pattern from each other and the patterns may be presented randomly.

In this case, in step S400 in which the computer receives the identification input about the second object and the third object from the response input device of the subject, the identification input includes an input about whether the second object 20 and the third object 30 have the same pattern or different patterns, or whether the object presented in the defect region has the horizontal or the vertical pattern.

In another embodiment, the second object 20 and the third object 30 may be rotating, and the rotation directions of the second object 20 and the third object 30 may be the same or different from each other and may be random.

In this case, in step S400 in which the computer receives the identification input about the second object and the third object from the response input device of the subject, the identification input includes an input about whether the second object 20 and the third object 30 rotate in the same direction, in different directions, or whether the object presented in the defect region rotates in a right, left, downward, or upward direction.

In still another embodiment, the depths on the screen at which the second object 20 and the third object 30 are presented may be the same as or different from each other and may be random. In this connection, the depth at which each of the second object 20 and the third object 30 is presented refers to a distance between each of the second object 20 and the third object 30 and the screen recognized by the subject.

In this case, in step S400 in which the computer receives the identification input about the second object and the third object from the response input device of the subject, the identification input includes an input whether the second object 20 and the third object 30 are presented at the same depth or at different depths, or whether the object presented in the defect region is presented at a larger depth or a smaller depth than the object presented in a non-defect region is.

The type of the stimulus of the second object 20 and the third object 30 varies depending on the region in which the visual field defect occurs in the brain. Thus, this will be described in detail in FIGS. 7A to 7C.

In step S300 of the presenting, by the computer, of the second object 20 and the third object 30 on the screen after the first object 10 is divided and presented or removed, one embodiment of presenting the second object 20 and the third object 30 after the first object 10 is divided and presented or removed may include an embodiment in which after the first object 10 is divided into the first divided object 60 and the second divided object 70, and then when the first divided object 60 and the second divided object 70 reach the predetermined region, the first divided object 60 and the second divided object 70 are changed into the second object 20 and the third object 30 respectively, which in turn are presented to the subject.

The division of the first object 10 into the first divided object 60 and the second divided object 70 may be made within a predetermined time.

The predetermined time is set to be as short as possible. When the predetermined time is short, a following advantage is achieved: when the first object 10 is divided into the first divided object 60 and the second divided object 70 in the central visual field and then the first divided object 60 and the second divided object 70 are changed into the second object 20 and the third object 30, respectively, the second object 20 and the third object 30 may be presented such that the subject may view the second object 20 and the third object 30 while the subject's gaze is not moved and is continuously fixed to the central visual field. A depth of a region in which the third object 30 is presented may be the same as or different from a depth of a region in which the second object 20 is presented.

Determining, by the subject, whether the shapes of the second object 20 and the third object 30 are identical with each other, or what shape of an object in the visual field defect region is a purpose of the visual field defect-ameliorating training of the inventive concept. Thus, presenting the second object 20 and the third object 30 before the second object 20 and the third object 30 reach the visual field defect region may not achieve a significant effect on the training.

Thus, when the first object 10 approaching in the flying manner is divided into the first divided object 60 and the second divided object 70 and, then, the first divided object 60 and the second divided object 70 reach the predetermined region, the first divided object 60 and the second divided object 70 may be changed into the second object 20 and the third object 30, respectively, in the region in which the second object 20 and the third object 30 should be presented for the visual field defect-ameliorating training or in the surrounding region around the region in which the second object 20 and the third object 30 should be presented for the visual field defect-ameliorating training.

As described above, in one embodiment the predetermined region may refer to a region in which the first divided object 60 and the second divided object 70 are changed into the second object 20 and the third object 30, respectively.

In another embodiment, the predetermined region refers to a region which the first divided object 60 and the second divided object 70 reach in the flying manner, and which has a depth larger than a depth of a region in which the second object 20 or the third object 30 is presented.

The detailed description of the manner in which the first object 10 is divided into the first divided object 60 and the second divided object 70 which in turn are changed into the second object 20 and the third object 30 respectively refers to descriptions of FIGS. 4A and 4B and FIGS. 5A and 5B to be described later.

In step S300 of presenting the second object 20 and the third object 30, the presentation of the second object 20 and the third object 30 may vary based on a difficulty level of the training.

In one embodiment, a contrast of each of the second object 20 and the third object 30 may be adjusted. When the subject correctly answers the form of the stimulus of each of the second object 20 and the third object 30, the computer may lower the contrast to increase the difficulty level. To the contrary, when the subject incorrectly answers the form of the stimulus of each of the second object 20 and the third object 30, and incorrect answers are continuous, the computer may raise the contrast to lower the difficulty level.

In another embodiment, a size of each of the second object 20 and the third object 30 may be adjusted. When the subject correctly answers the form of the stimulus of each of the second object 20 and the third object 30, the computer may decrease the size to increase the difficulty level. To the contrary, when the subject incorrectly answers the form of the stimulus of each of the second object 20 and the third object 30, and incorrect answers are continuous, the computer may increase the size to lower the difficulty level.

In another embodiment, an exposure time duration of the second object 20 and the third object 30 may be adjusted. When the subject correctly answers the form of the stimulus of each of the second object 20 and the third object 30, the computer may decrease the exposure time duration to increase the difficulty level. To the contrary, when the subject incorrectly answers the form of the stimulus of each of the second object 20 and the third object 30, and incorrect answers are continuous, the computer may increase the exposure time duration to lower the difficulty level.

In still another embodiment, a location of each of the second object 20 and the third object 30 may be adjusted.

The step S300 of presenting the second object and the third object may include presenting the second object 20 and the third object 30 within a visual field range of the subject. In this connection, an angle between the central visual field and the location in which each of the second object 20 and the third object 30 is presented may be adjusted.

In one embodiment, the angle adjustment may be performed based on the visual field defect region of the subject. In other embodiments, the angle may be adjusted such that the training proceeds step by step depending on a treatment condition.

The step S400 in which the computer receives the identification input about the second object and the third object from the response input device of the subject may include a step in which the computer receives an input from the subject about whether the second object 20 and the third object 30 are the same or different from each other in terms of the presentation manners of the second object 20 and the third object 30 as described above, or what presentation manners thereof.

Even before the second object and the third object has been presented for a predetermined time in step S300 in which after the first object 10 is divided and presented or removed, the computer presents the virtual second object and the virtual third object on the screen, the computer may receive the identification input about the second object and the third object from the subject's response input device S400.

That is, the computer may present the second object and the third object on the screen and simultaneously receive the identification input about the second object and the third object from the subject's response input device.

In one embodiment of the input manner, the subject may press different buttons based on different answers. In another embodiment of the input manner, the subject may vary the number of times of pressing the same button based on different answers. However, the present disclosure is not limited to the embodiment. The input manner may include any manner in which the subject answers a question using the subject's response input device.

In accordance with the inventive concept, the computer may continuously present the second object 20 and the third object 30 as the stimulus in the central visual field and/or the non-central visual field while the subject uses the first object 10 moving in the approaching manner to fix the subject's gaze direction to the central visual field.

The computer may present the second object 20 and the third object 30 in various manners, such that the training may be implemented as a game for the subject, thereby to induce interest of the subject in the visual field defect-ameliorating training.

Figure 2:
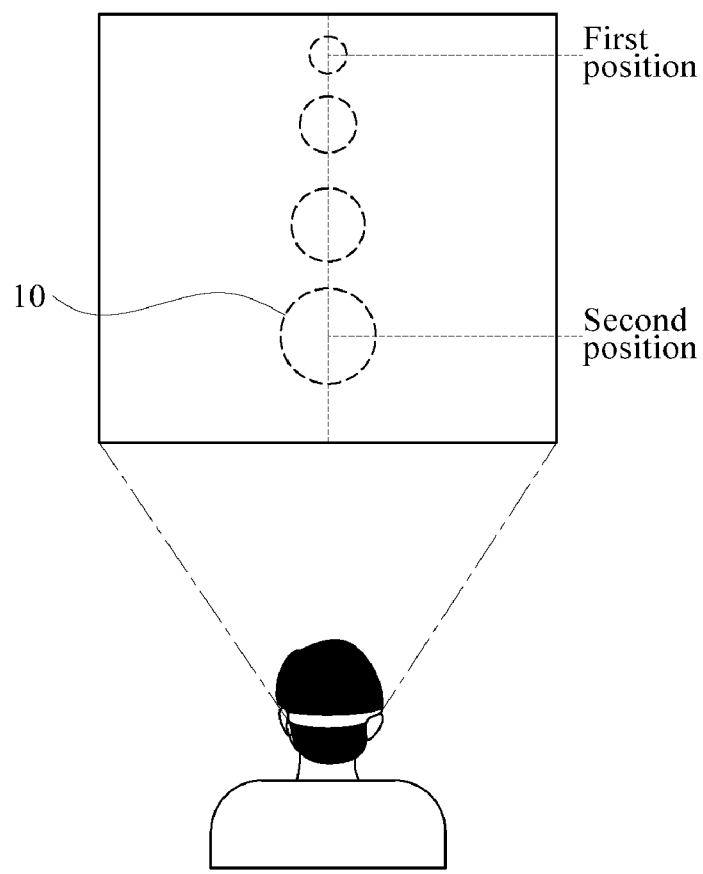
FIG. 2 is a view showing a screen viewed from above on which a first object is presented in an approaching manner from a first position to a second position.
Figure 3:
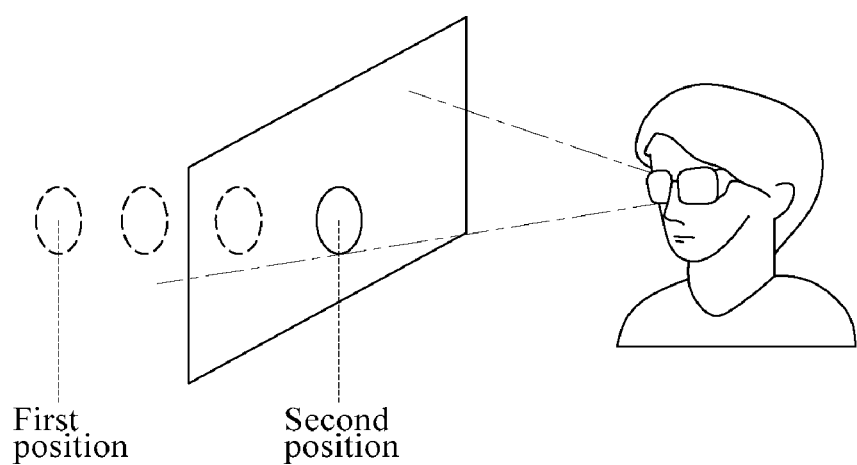
FIG. 3 is a view showing a visual field defect-ameliorating training screen viewed from a side.

FIG. 2 is a view showing a screen viewed from above on which a first object is presented in an approaching manner from a first position to a second position;

FIG. 3 is a view showing a visual field defect-ameliorating training screen as viewed from a side.

Referring to FIG. 2 and FIG. 3, it may be identified that the first object 10 approaches from the first position to the second position on the screen within the visual field range of the subject.

As described above, the first position is a position at which the change of the position, the size or the shape of the first object 10 starts. The second position is the position at which the change of the position, the size or the shape of the first object 10 is completed.

In an embodiment, when the first object 10 moves in a virtual space, the first position is positioned at a greater distance on the screen from the subject than the second position is.

In another embodiment, when the size of the first object 10 is changed in a single position, the first position and the second position may be the same.

In addition, the first position and the second position are on the central visual field of the subject. The first object 10 is presented in the approaching manner from the first position to the second position. This may improve the subject's concentration.

FIGS. 4A and 4B and FIGS. 5A and 5B are views showing the visual field defect-ameliorating training screen as viewed from a front.

Figure 4A:
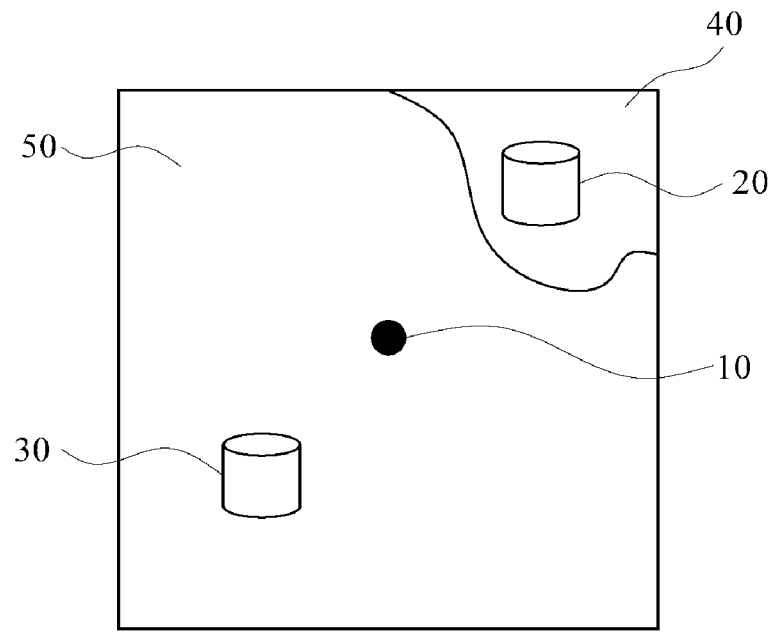
FIGS. 4A and 4B and FIGS. 5A and 5B are views showing a visual field defect-ameliorating training screen viewed from a front.
Figure 4B:
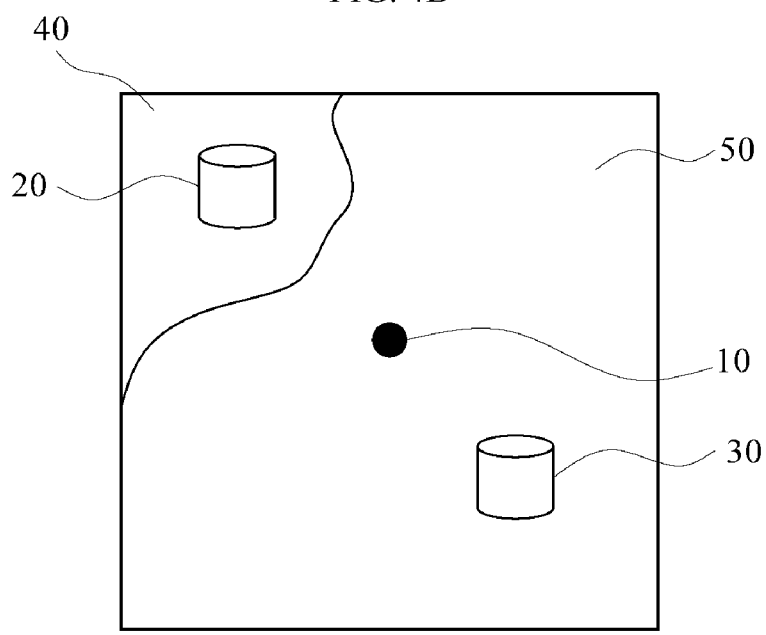

FIGS. 4A and 4B show that the second object and the third object are arranged in different positions in a diagonal direction with respect to the central visual field.

Further, in FIGS. 4A and 4B, the second object and the third object are respectively arranged in a defect region 40 and a normal region 50 as arranged diagonally to each other. However, as described above, the second object and the third object may be arranged diagonally to each other only in the normal region 50. In this case, the second object 20 may be disposed in the normal region 50.

Figure 5A:
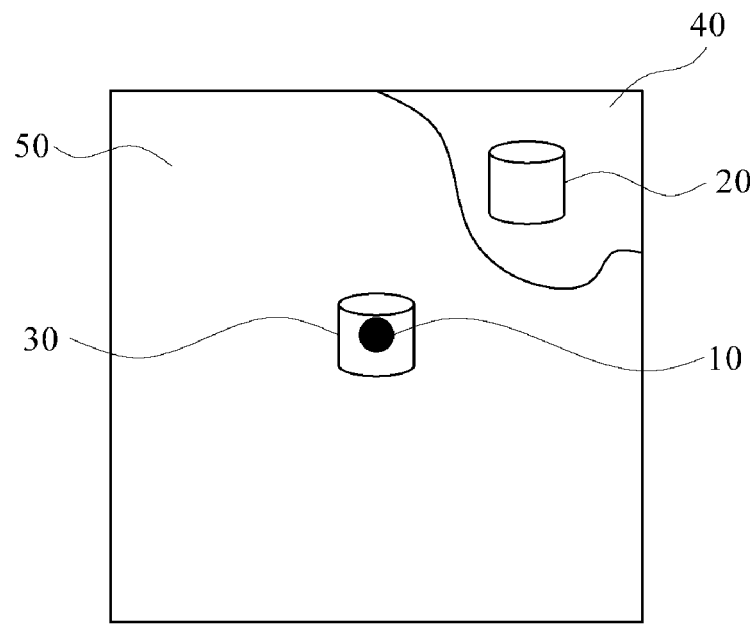
Figure 5B:
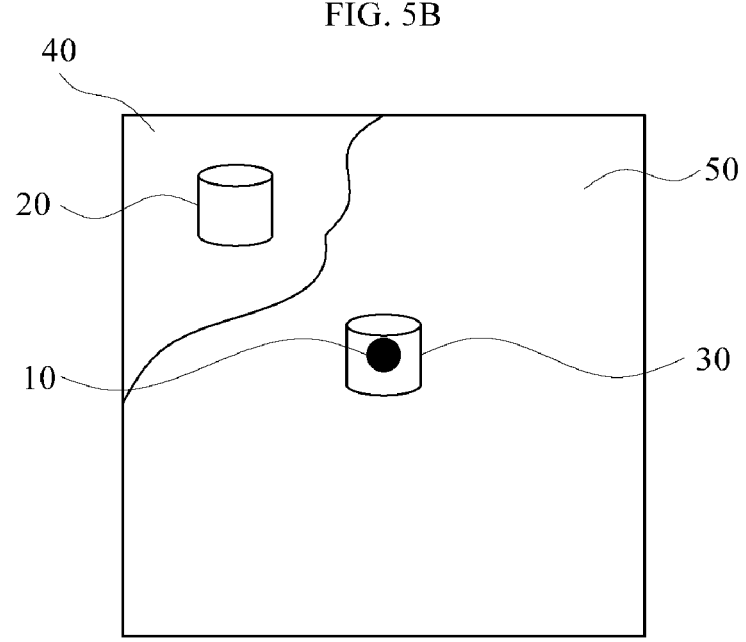

FIGS. 5A and 5B show the arrangement of the second object and the third object in the central visual field region and the defect region.

Referring to FIGS. 4A and 4B and FIGS. 5A and 5B, the visual field defect-ameliorating training screen includes the first object 10, the second object 20, the third object 30, the visual field defect region 40 and the normal region 50.

In FIGS. 4A and 4B and FIGS. 5A and 5B, the first object 10 is shown. However, as described above, the first object 10 may be removed while the second object 20 and the third object 30 are created. The first object 10 may be removed, and the second object 20 and the third object 30 may be presented.

Further, after the first object 10 is divided into the first divided object 60 and the second divided object 70, the first divided object 60 and the second divided object 70 may be removed and instead the second object 20 and the third object 30 may be created. Alternatively, the first divided object 60 and the second divided object 70 may be changed into the second object 20 and the third object 30 respectively.

Referring to FIGS. 4A and 4B, the second object 20 is disposed in the visual field defect region 40, and the third object 30 is disposed in the normal region 50 in a diagonal direction to the second object 20 with respect to the central visual field. However, one of the second object 20 and the third object 30 may be placed on the visual field defect region 40 and the other thereof may be placed on the normal region 50.

Referring to FIGS. 5A and 5B, the second object 20 is disposed in the visual field defect region 40, the third object 30 is disposed in the central visual field. However, one of the second object 20 and the third object 30 may be placed in the visual field defect region 40 and the other thereof may be placed in the central visual field.

The visual field defect-ameliorating training may be performed by the subject determining whether a shape of the stimulus of the object presented in the normal region 50 or the central visual field is identical with a shape of the stimulus of the object presented in the defect region 40, or what shape of the stimulus of the object presented in the defect region 40.

FIGS. 6A to 6C and 7A to 7C are diagrams for describing a continuous state in which the first object 10, the second object 20 and the third object 30 move on the screen.

Figure 6A:
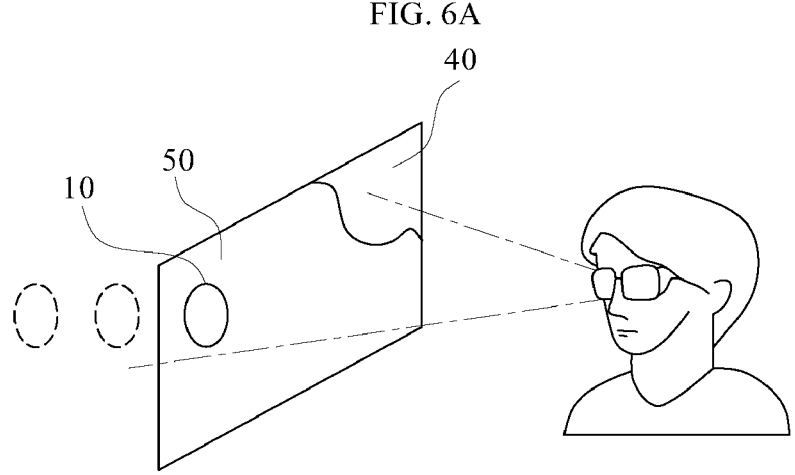
FIGS. 6A to 6C and 7A to 7C are diagrams for describing a continuous state in which a first object 10, a second object 20, and a third object 30 move on a screen.
Figure 6B:
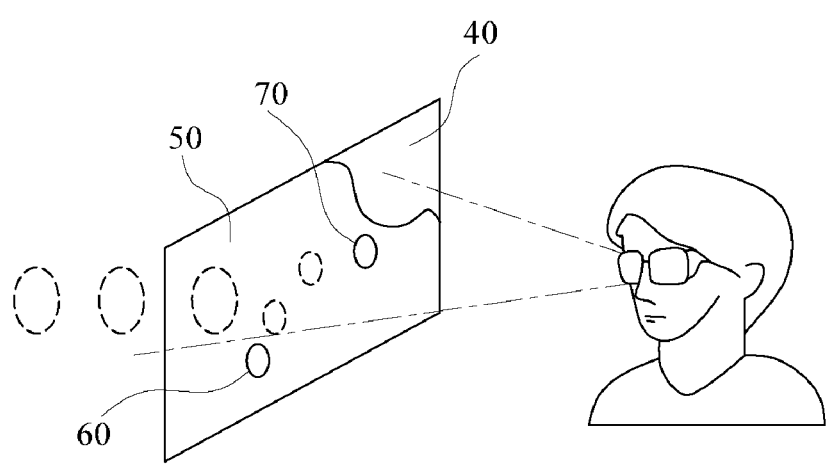
Figure 6C:
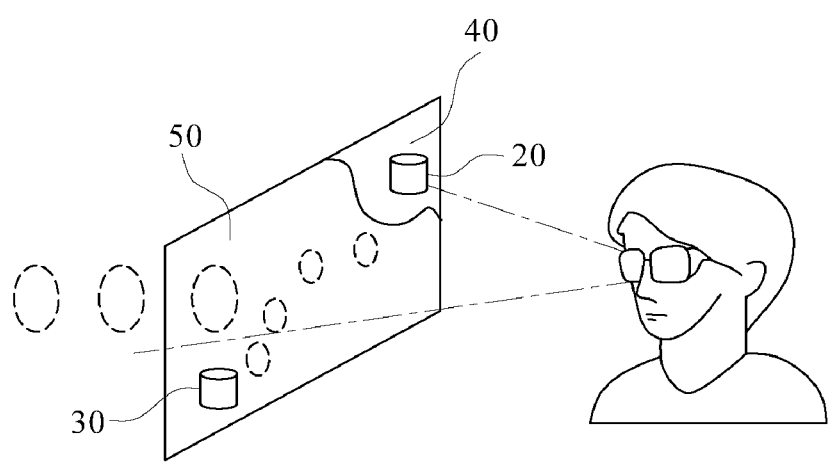
Figure 7A:
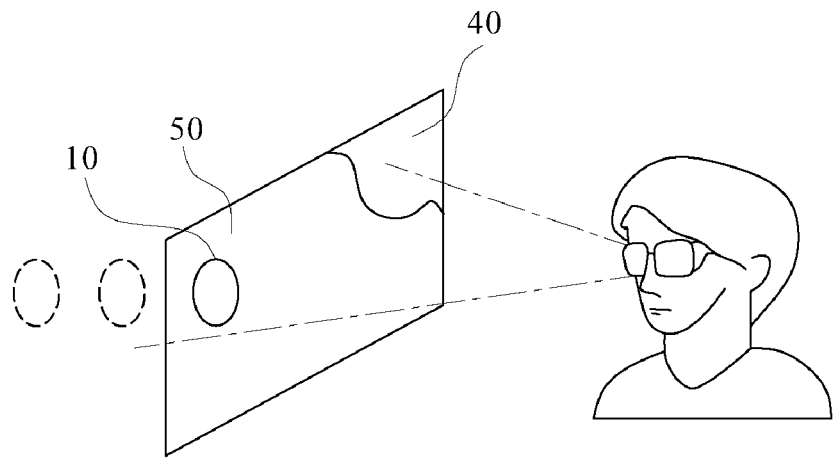
Figure 7B:
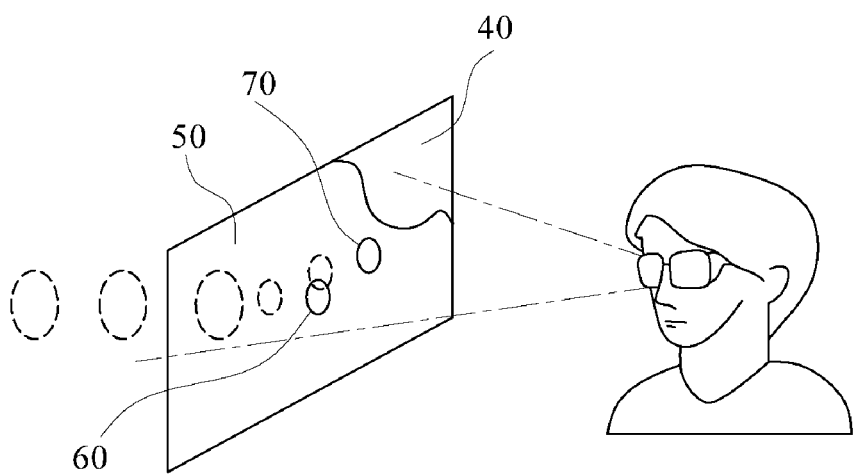
Figure 7C:
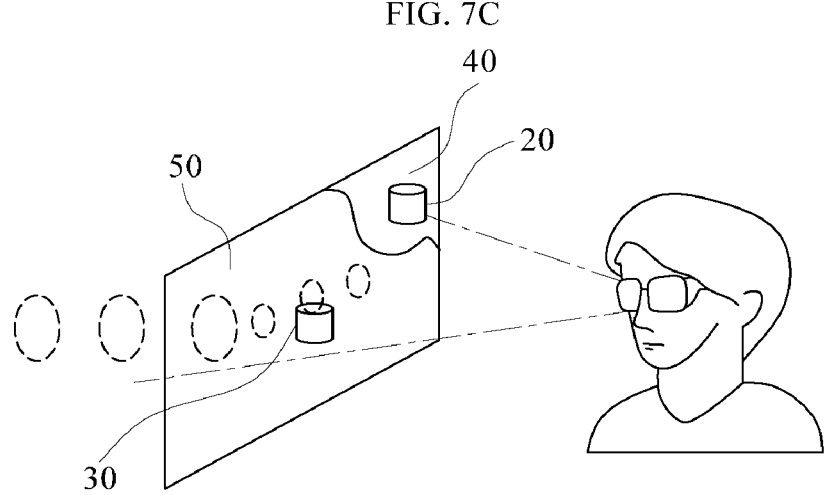
Figure 8A:
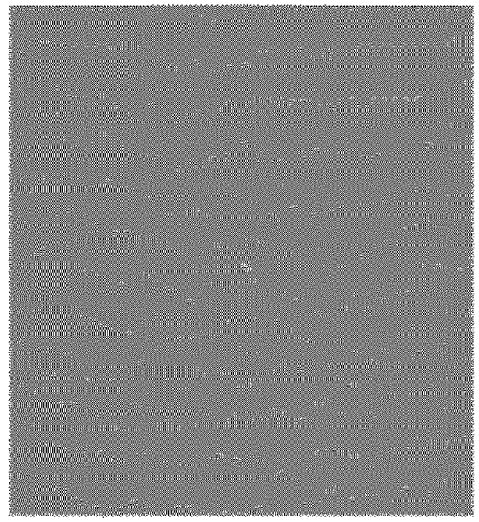
FIGS. 8A to 8F and FIGS. 9A to 9F are views showing that a first object 10, a second object 20, and a third object move on an actually implemented screen.
Figure 8B:
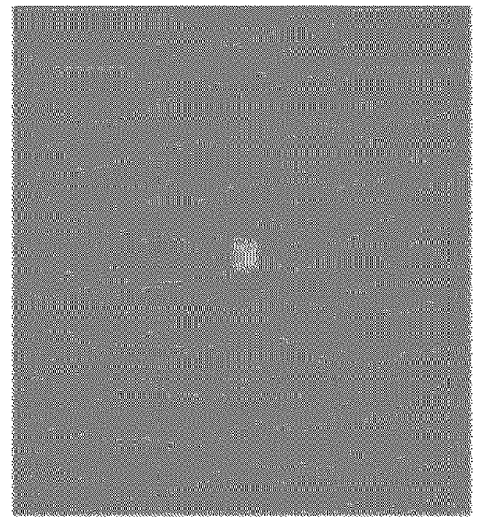
Figure 8C:
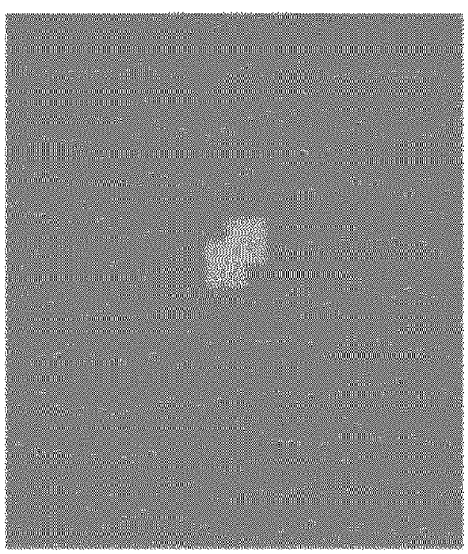
Figure 8D:
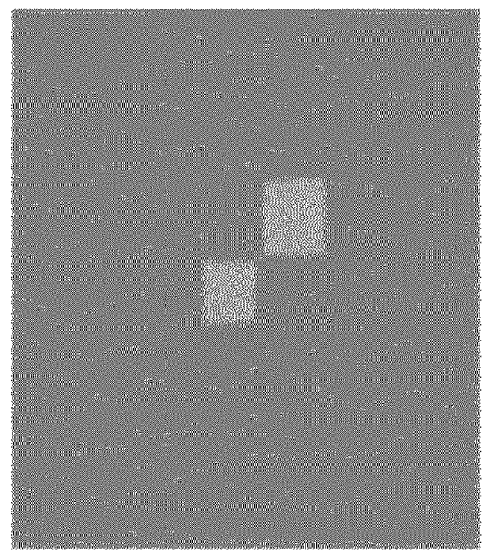
Figure 8E:
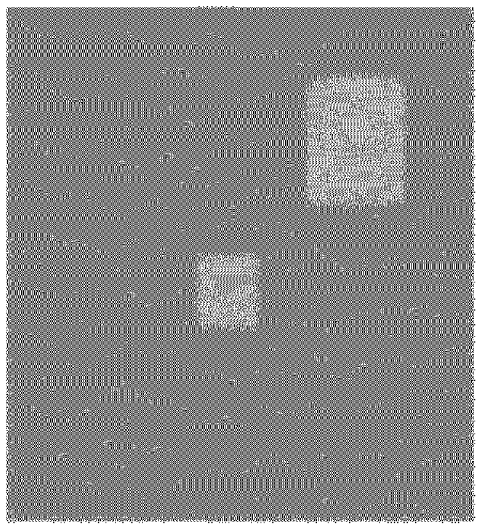
Figure 8F:
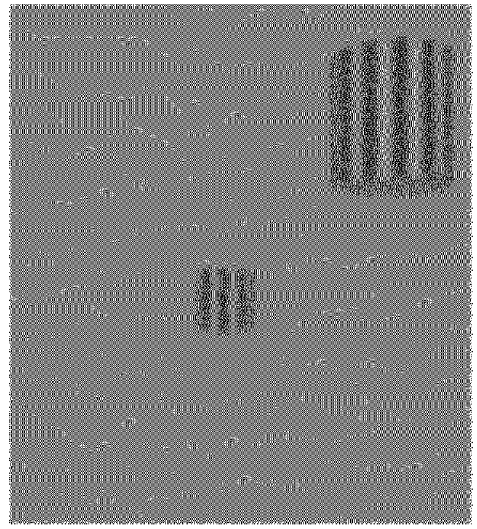
Figure 9A:
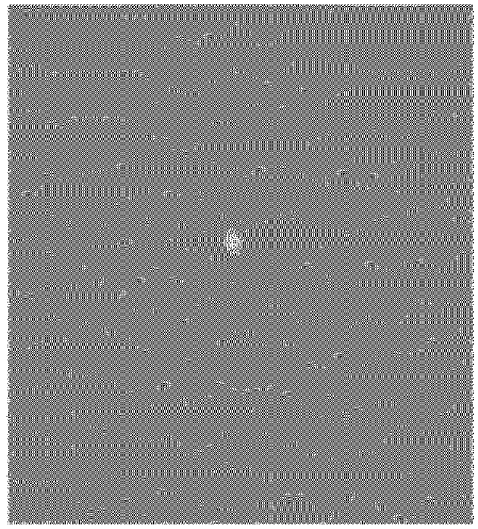
Figure 9B:
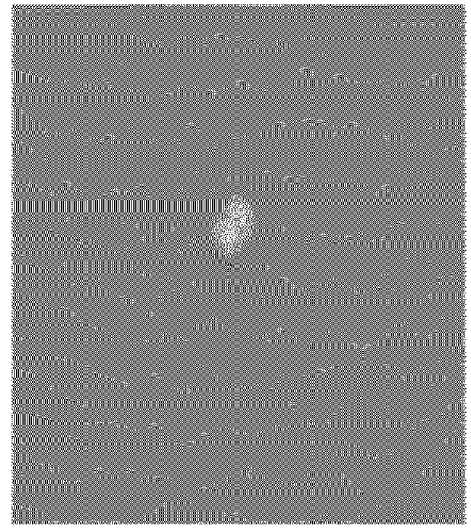
Figure 9C:
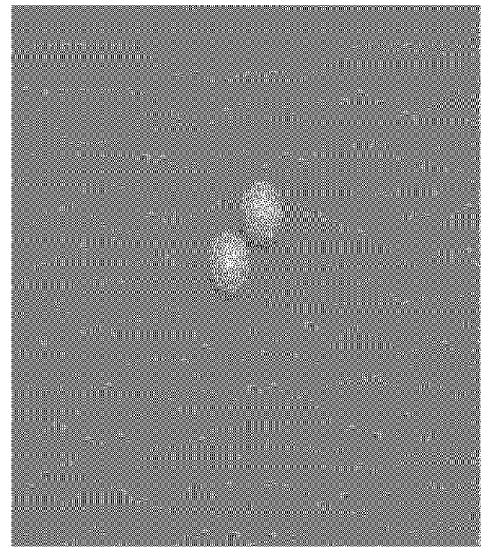
Figure 9D:
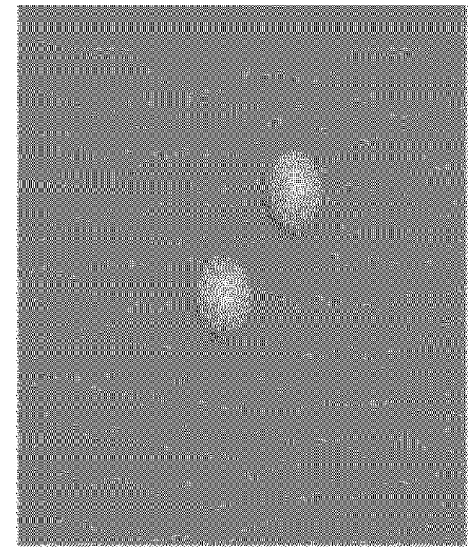
Figure 9E:
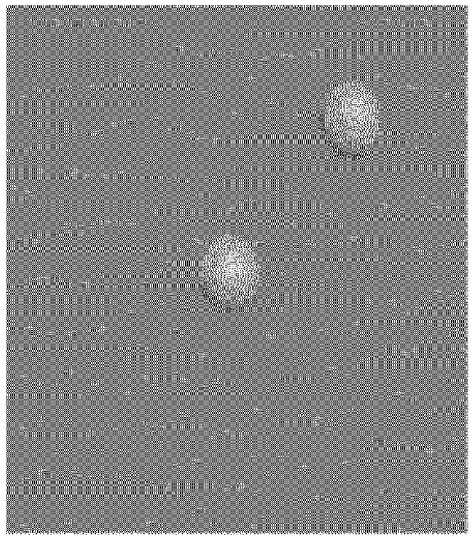
Figure 9F:
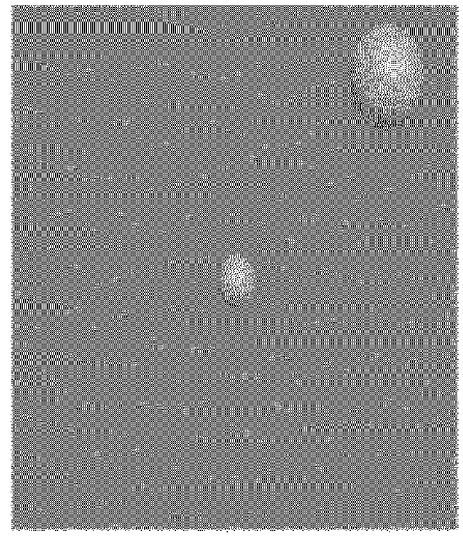

FIGS. 6A to 6C are diagrams showing a time flow from FIGS. 6A to 6C. FIGS. 7A to 7C are diagrams showing a time flow from FIGS. 7A to 7C.

FIGS. 6A to 6C and FIGS. 7A to 7C respectively include visual field defect-ameliorating trainings performed on a two-dimension screen and a three-dimension screen using VR.

When the visual field defect-ameliorating training is performed on a screen in a three-dimension using VR, the object is presented in a flying manner from a distant position to the subject when viewed from the subject's point of view.

When the visual field defect-ameliorating training is performed on a two-dimension screen, the object is presented in a changing manner from a small size to a larger size. Thus, the object is presented to the subject in a visually flying manner.

The embodiments of the present specification may include the embodiment in which the visual field defect-ameliorating training is performed on a screen in a three-dimension using VR, such that the object is presented in a flying manner from a distant position to the subject, and the embodiment in which the visual field defect-ameliorating training is performed on a two-dimension screen, such that the object is presented in a changing manner from a small size to a larger size and thus is presented to the subject in a visually flying manner.

Referring to FIG. 6A and FIG. 7A, first, the first object 10 moves from the first position to the second position on the screen as shown in FIG. 3. As described above, the first position and the second position are on the central visual field of the subject, and the first object 10 is presented in the approaching manner from the first position to the second position on the three-dimension screen using VR, thereby to induce the subject's concentration.

After, as shown in FIG. 6A and FIG. 7A, the first object 10 reaches the second position, the first object 10 at the second position is divided into the first divided object 60 and the second divided object 70 arranged in a diagonal direction referring to FIG. 6B. Then, referring to FIG. 7C, the first divided object 60 moves toward the central visual field, and the second divided object 70 moves toward the defect region.

In FIG. 6B and FIG. 7B, the first object 10 at the second position is divided into the first divided object 60 and the second divided object 70 which in turn move. Alternatively, the first object 10 may be removed in the scattered manner from the second position, or may be removed in the spreading manner from the second position. While the first object 10 is scattered or spread from the second position, a presented depth of the first object 10 as scattered or spread may be adjusted. The first object 10 at the second position may be divided into the first divided object 60 and the second divided object 70 which in turn move. In this connection, a presented depth of each of the divided first divided object 60 and the second divided object 70 may be adjusted.

In an embodiment, the first object 10 may be removed in the scattering or spreading manner from the second position and at the same depth.

That is, the first object 10 begins to be divided or scattered from the second position and at the same depth when viewed from the subject's perspective. The second object 20 and the third object 30 are arranged in the visual field defect region 40 and the normal region 50 or in the visual field defect region 40 and the central visual field, respectively, without adjusting the depth thereof.

In another embodiment, in the process of scattering or spreading the first object 10, the presented depth of the first object 10 as scattering or spreading on the two-dimension or three-dimension may be adjusted to be smaller than a depth thereof at the second position.

In another embodiment, when the first object 10 is divided into the first divided object 60 and the second divided object 70 which in turn move, a presented depth of each of the first divided object 60 and the second divided object 70 as moving on the two-dimension or three-dimension may be equal to the depth thereof at the second position.

In another embodiment, when the first object 10 is divided into the first divided object 60 and the second divided object 70 which in turn move, a presented depth of each of the first divided object 60 and the second divided object 70 as moving on the two-dimension or three-dimension may be adjusted to the smaller than the depth thereof at the second position.

That is, the first object 10 starts to be divided, scattered, or spread from the second position and at the depth thereof at the second position. Then, the depth at which the first object 10 as divided or the first divided object 60 and the second divided object 70 as moving are presented may be smaller than the depth thereof at the second position.

The manner in which the first object 10 is scattered or spread may be applied in the same manner as described above in the description of FIG. 1.

Therefore, when viewed from the perspective of the subject, the first object 10 may be separated from the second position and gradually approach toward the subject such that the second object 20 and the third object 30 may be disposed in the visual field defect region 40 and the normal region 50, or the visual field defect region 40 and the central visual field, respectively. Alternatively, when viewed from the perspective of the subject, the first object 10 may be divided into the first divided object 60 and the second divided object 70 which in turn may gradually approach toward the subject, which in turn may be changed to the second object 20 and the third object 30, respectively, in the visual field defect region 40 and the normal region 50, or the visual field defect region 40 and the central visual field, respectively.

In FIG. 6B and FIG. 7B, the presented depth of the first object 10 at the second position where the first object 10 is placed before being divided may be larger than the presented depth of each of the first divided object 60 and the second divided object 70 as being divided.

Referring to FIG. 6C, the first object 10 at the second position may be divided into the first divided object 60 and the second divided object 70 arranged and moving in the diagonal direction as shown in FIG. 6B. Alternatively, the first object 10 at the second position may be removed in a scattered manner or in a spreading manner, and then, the second object 20 may be disposed in the visual field defect region 40, and the third object 30 may be disposed in the normal region 50 such that the second object 20 and the third object 30 may be arranged in the diagonal direction with respect to the central visual field.

Further, referring to FIG. 7C, the first object 10 at the second position may be removed in a scattered manner or in a spreading manner, or may be divided into the first divided object 60 and the second divided object 70 arranged and moving in the diagonal direction as shown in FIG. 7B, and then the second object 20 may be placed in the visual field defect region 40 and the third object 30 may be placed in the central visual field.

In one embodiment, the depth at which each of the second object 20 and the third object 30 is presented may be equal to the presented depth of the first object 10 at the second position.

In another embodiment, the depth at which each of the second object 20 and the third object 30 is presented may be smaller than the presented depth of the first object 10 at the second position.

Referring to FIGS. 6A to 6C and FIGS. 7A to 7C, the process in which the first object 10 is divided into the first divided object 60 and the second divided object 70, and then the first divided object 60 and the second divided object 70 are changed into the second object 20 and the third object 30, and an effect of the process will be generally described below.

As described above, the first object 10 approaches toward the subject from the first position to the second position, and the first object 10 at the second position is divided into the first divided object 60 and the second divided object 70. Then, the divided first divided object 60 and the second divided object 70 approach toward the subject from the second position to the predetermined region in a direction in which the second object 20 and the third object 30 will be arranged. Then, the first divided object 60 and the second divided object 70 are replaced with the virtual second object 20 and the virtual third object 30, respectively, in the predetermined region, which in turn are presented to the subject.

In this connection, the predetermined region may be a region in which each of the second object 20 and the third object 30 should be placed for visual field defect-ameliorating training, or a surrounding region around the region in which each of the second object 20 and the third object 30 should be placed for visual field defect-ameliorating training.

In one embodiment, when the first divided object 60 and the second divided object 70 reach the region in which each of the second object 20 and the third object 30 should be placed for visual field defect-ameliorating training, the second object 20 and the third object 30 may be presented on the region to the subject.

In another embodiment, when the first divided object 60 and the second divided object 70 reach the surrounding region around the region in which each of the second object 20 and the third object 30 should be placed for visual field defect-ameliorating training, the second object 20 and the third object 30 may be presented on the region in which each of the second object 20 and the third object 30 should be placed for visual field defect-ameliorating training.

Further, the division of the first object 10 into the first divided object 60 and the second divided object 70 may be made within a predetermined time.

In this connection, the predetermined time is set to be as short as possible. When the predetermined time is short, a following advantage is achieved: when the first object 10 is divided into the first divided object 60 and the second divided object 70 in the central visual field and then the first divided object 60 and the second divided object 70 are changed into the second object 20 and the third object 30, respectively, the second object 20 and the third object 30 may be presented such that the subject may view the second object 20 and the third object 30 while the subject's gaze is not moved and is continuously fixed to the central visual field.

Among depths of regions in which the second object 20 and the third object 30 are presented, a depth of a region in which the second object 20 is presented means a depth at which the second object 20 is presented in the visual field defect region because the region in which the second object 20 is presented corresponds to the visual field defect region.

A depth of a region in which the third object 30 is presented may be the same as or different from a depth of a region in which the second object 20 is presented.

Determining, by the subject, whether the shapes of the second object 20 and the third object 30 are identical with each other, or what shape of an object in the visual field defect region is a purpose of the visual field defect-ameliorating training of the inventive concept. Thus, presenting the second object 20 and the third object 30 before the second object 20 and the third object 30 reach the visual field defect region may not achieve a significant effect on the training.

Thus, when the first object 10 approaching in the flying manner is divided into the first divided object 60 and the second divided object 70 and, then, the first divided object 60 and the second divided object 70 reach the predetermined region, the first divided object 60 and the second divided object 70 may be changed into the second object 20 and the third object 30, respectively, in the region in which the second object 20 and the third object 30 should be presented for the visual field defect-ameliorating training or in the surrounding region around the region in the second object 20 and the third object 30 should be presented for the visual field defect-ameliorating training.

FIGS. 8A to 8F and 9A to 9F are views showing movement of the first object 10, the second object 20 and the third object 30 on the actually implemented screen.

FIGS. 8A to 8F are shown to the subject in an order of FIGS. 8A to 8F. FIGS. 9A to 9F are shown to the subject in an order of FIGS. 9A to 9F. FIGS. 8A to 8F and 9A to 9F may be applied to the screens implemented in the two-dimension and three-dimension, respectively.

Figure 10:
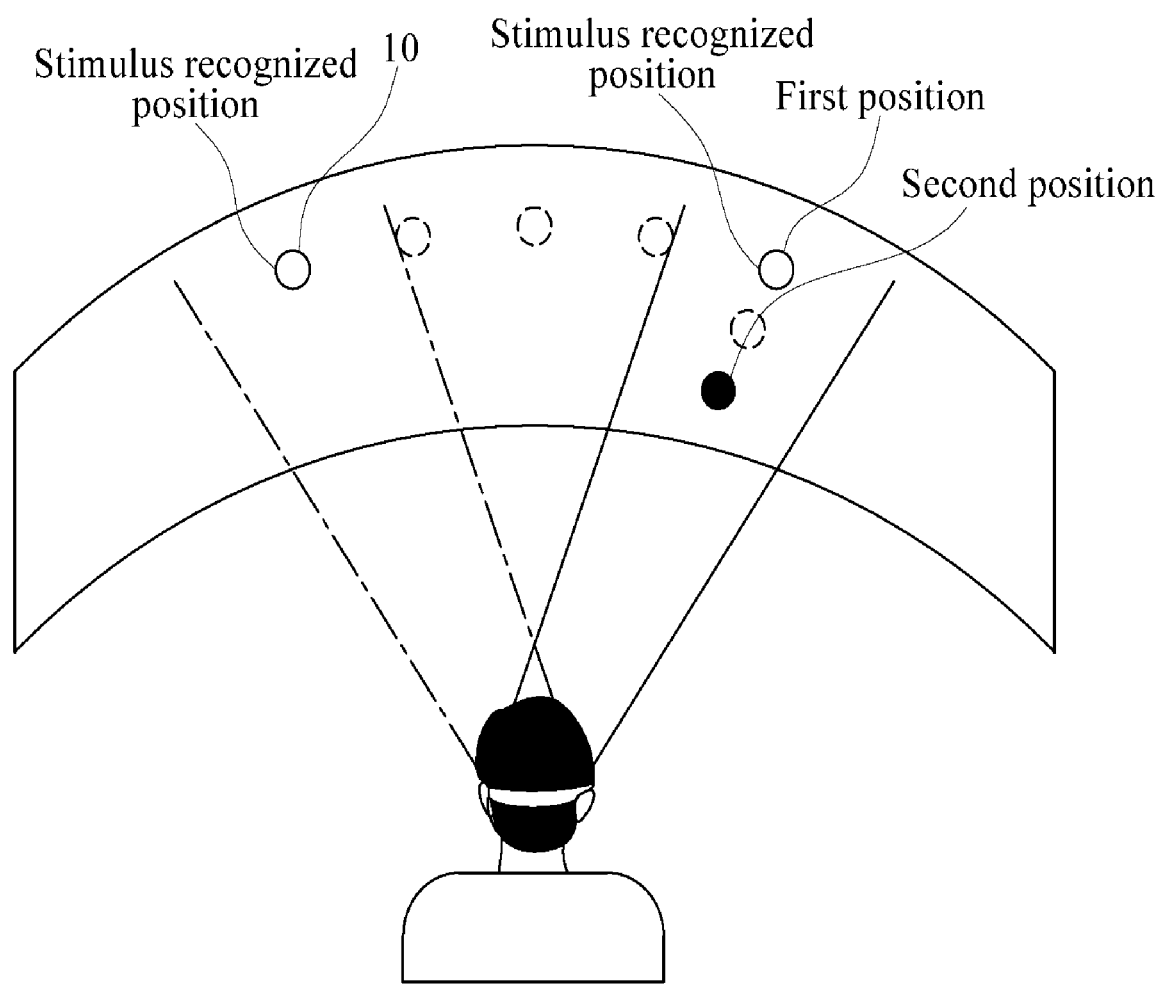
FIG. 10 is a diagram for describing that a first object is presented in a displaced manner such that a subject changes a direction of a central visual field thereof toward the displaced first object.

FIG. 10 is a diagram for explaining that the first object is presented after the first object is displaced to change a direction of the central visual field of the subject.

FIG. 10 shows that the subject wearing a head mounted display performs the visual field defect-ameliorating training in a three-dimension space.

Unlike the visual field defect-ameliorating training in the two-dimension, all directions of 360° may be used in the three-dimension space. Therefore, a point at which the first object 10 starts to move may be changed in the three-dimension space.

Referring to FIG. 10, it may be identified that the stimulus recognized position of the first object 10 is displaced from left to right.

When it is identified that the subject wearing the head mounted display keeps an eye on the first object 10 at the right stimulus recognized position as displaced to the right, the computer presents the first object 10 such that the first object moves in an approaching manner to the subject from the first position to the second position in the virtual space. In this way, the training stimulus may be applied to the subject.

A scheme for identifying the gaze of the subject wearing the head mounted display toward the first object 10 at the displaced stimulus recognized position may include one embodiment in which it is determined whether there is the first object 10 at the displaced stimulus recognized position in the virtual space in a direction that the head mounted display gazes.

Further, in another embodiment, when the head mounted display includes an eye-tracking function, the gaze direction is calculated, and it is determined whether there is the first object 10 at the displaced stimulus recognized position in the virtual space in the gaze direction and the line of sight direction.

As described above, when the head mounted display includes an eye tracking function, and even when the head is toward the stimulus recognized position, but when a pupil is not toward the stimulus recognized position, it is determined that the subject does not gaze at the first object 10.

Accordingly, only when the head is toward the stimulus recognized position, and the pupil is toward the stimulus recognized position, it is determined that the subject gaze at the first object 10.

A scheme for recognizing the gaze direction of the head mounted display may involve recognizing the direction using a sensor. A type of the sensor may include a motion detection sensor including gyro sensors, and acceleration sensors, and direction detection sensors.

The stimulus recognized position to which the first object 10 is displaced may be in a dot form, and the subject gaze direction may be changed as the subject gaze direction moves sequentially from a direction toward the previous position to a direction toward the displaced position.

When the subject does not concentrate during the training, the visual field is blurred. As the visual field is blurred, the visual stimulus presented in the non-central visual field region may not be recognized by the subject.

Therefore, according to the inventive concept, the computer may present the first object 10 while changing the stimulus recognized position in the three-dimension space, thereby to allow the subject to focus on the training and thus to prevent the subject from missing the visual stimulus that may be actually perceived, thereby to increase the accuracy of the training result.

Figure 11:
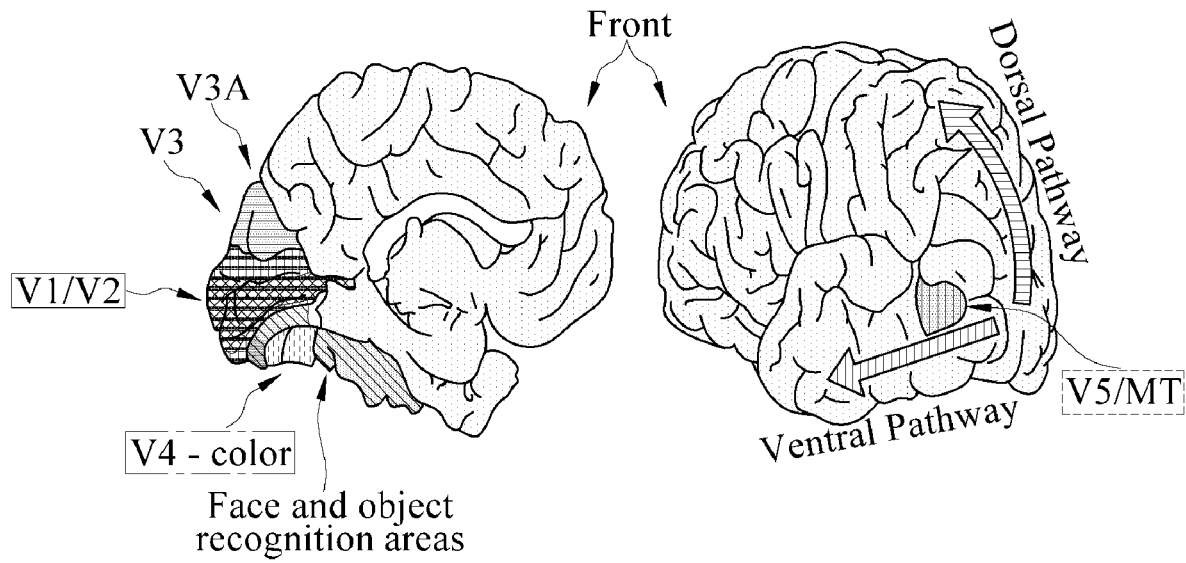
FIG. 11 is a diagram for describing a type of stimulus that varies depending on a region where visual field defect occurs.

FIG. 11 is a diagram for describing various types of stimulus applied to stimulate each region responsible for visual perception in the brain.

Referring to FIG. 11, it may be identified that regions in charge of visual perception are shown in a distinguished manner.

When the computer presents various forms of stimulus, not only the defect occurring region itself may be ameliorated, but also the blindsight in which what is not visible due to damage of the defect occurring region is visible to the subject via training of a region other than the defect-occurring region may be trained.

A V1 region of FIG. 11 refers to a region that recognizes a difference between horizontal and vertical lines. Thus, the V1 region may be stimulated by presenting the second object 20 and the third object 30 in the horizontal pattern and/or the vertical pattern.

A V4 region of FIG. 11 refers to a region that recognizes a color, a depth and a shape. Thus, the V4 region may be simulated by presenting the second object 20 and the third object 30 to have the same or different rotation directions, or by presenting the second object 20 and the third object 30 while the depth at which the second object 20 and the third object 30 are presented is adjusted.

A MT/V5 region of FIG. 11 refers to a region that recognizes a motion, a speed, and a direction. Thus, the MT/V5 region may be stimulated by presenting the second object 20 and the third object 30 to have the same or different rotation directions, or by presenting the second object 20 and the third object 30 while the depth at which the second object 20 and the third object 30 are presented is adjusted.

Further, the stimulus for the treatment of the visual defect may be presented as not only the visual stimulus as the second object 20 and the third object 30 on the screen, but also an auditory stimulus.

In one embodiment, when the subject does not well recognize that the second object 20 is presented in a region on the screen corresponding to the defect region, the auditory stimulus may be provided as a hint about a position at which the second object 20 is presented. For example, when the defect region is on the right, the auditory stimulus on the right may be presented together with the second object 20.

Figure 12:
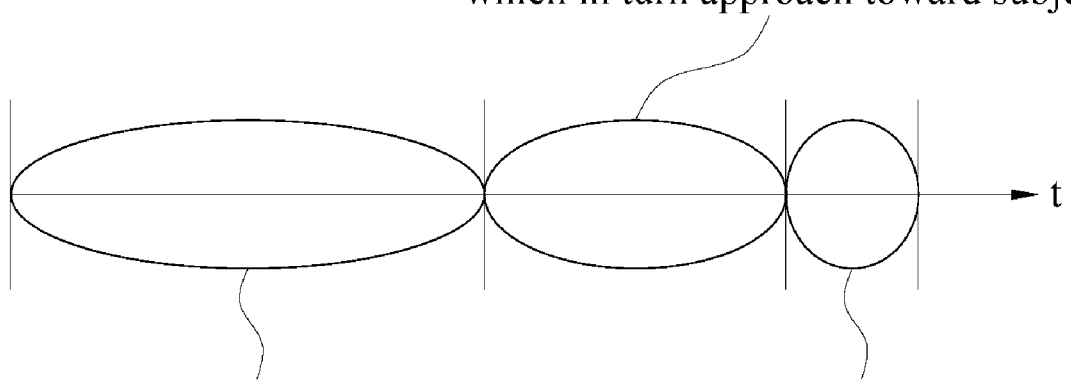
FIG. 12 is a diagram for describing controlling a presenting time of a first object, a second object, and a third object to adjust a difficulty level of visual field defect-ameliorating training.

FIG. 12 is a diagram for explaining how to control the presenting time duration of the first object, the second object, and the third object based on the difficulty level of the visual field defect-ameliorating training.

Referring to FIG. 12, FIG. 12 shows an event over time. A period in which the first object 10 moves refers to a time duration for which the first object moves from the first position to the second position.

In FIG. 12, a period in which the first object 10 is removed or the first object 10 is divided into the two objects which in turn approach toward the subject refers to a time duration for which the first object 10 at the second position is removed in various manners, or the first object 10 is divided into the first divided object 60 and the second divided object 70 which in turn approach toward the subject.

Therefore, a period after the period in which the first object 10 moves and before the time when the second object 20 and the third object 30 are presented may correspond to a period for which the first object 10 is removed, the first object 10 is divided into the two objects, or the first object 10 is spread.

After the period in which the first object 10 is removed or the first object 10 is divided into the two objects which in turn approach toward the subject, the second object 20 and the third object 30 are presented to the subject.

In one embodiment, for the period for which the first object 10 is removed or the first object 10 is divided into the two objects which in turn approach toward the subject, the first object 10 may be removed without the division thereof. In this case, the first object 10 may be removed and then the second object 20 and the third object 30 may be presented. In this connection, the first object 10 may be removed gradually or at once for the period for which the first object 10 is removed.

In another embodiment, for the period for which the first object 10 is removed or the first object 10 is divided into the two objects which in turn approach toward the subject, the first object 10 may be divided into the two objects which in turn approach toward the subject. In this case, the first object 10 may be divided into the first divided object 60 and the second divided object 70 which in turn may be presented in an approaching manner to the subject on the visual field of the subject. Then, when it is a time at which the second object 20 and the third object 30 should be presented, and when each of the first divided object 60 and the second divided object 70 reaches a region in which the second object 20 and the third object 30 should be presented, the first divided object 60 and the second divided object 70 may be removed and instead, the second object 20 and the third object 30 may be presented, or the first divided object 60 and the second divided object 70 may be changed to the second object 20 and the third object 30, respectively, which may be presented to the subject.

The periods shown in FIG. 12 may be adjusted based on a state of the subject, such that the subject's visual field defect treatment may be effectively performed.

Figure 13:
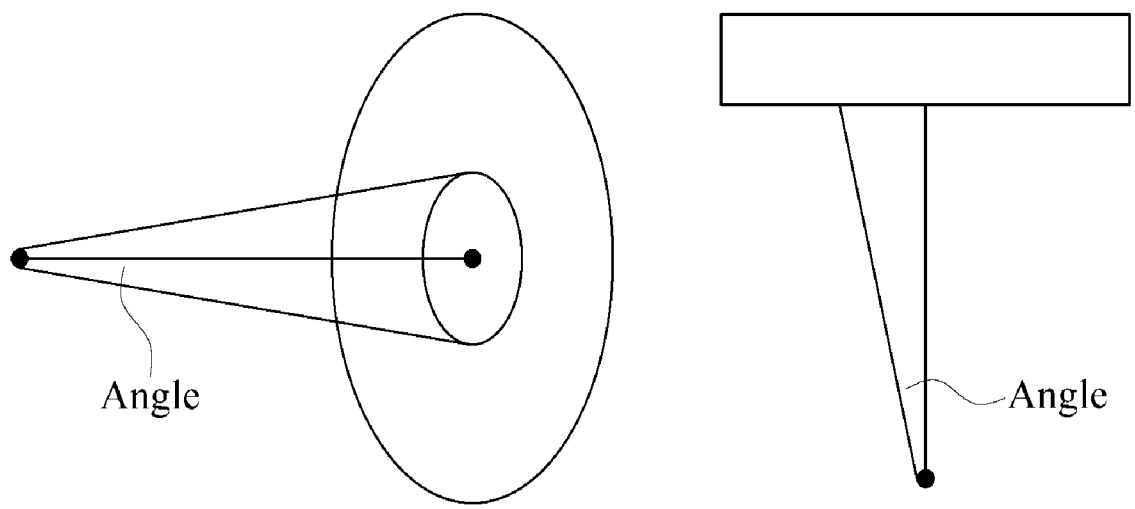
FIG. 13 is a diagram for describing adjustment of an angle of a visual field range in which a second object and a third object are presented.

FIG. 13 is a diagram for describing adjustment of an angle of a range of a visual field in which the second object and the third object are presented.

Referring to FIG. 13, when the second object 20 and the third object 30 are presented in the visual field defect region 40 and the normal region 50 respectively arranged diagonally to each other, the visual field range in which the second object 20 and the third object 30 are presented falls within a certain angular range around the central visual field.

When the angle is too small, a distance between the central visual field and each of the second object 20 and the third object 30 is small. Thus, the shapes of the second object 20 and the third object 30 may be recognized as being the same by the subject. Thus, the visual field defect-ameliorating training is not properly performed.

Therefore, the setting of the angle is important. Thus, it is preferable to set the angle to about 15°.

However, the angle is not fixed to 15°. However, there are situations in which training is possible only when the angle should be increased or decreased from 15° based on a state of each subject.

When the angle of the defect region of the subject around the central visual field is 15° or greater, the angle may be increased. To the contrary, when the angle of the defect region of the subject around the central visual field is smaller than 15°, the angle may be decreased.

A computing device for performing visual field defect-ameliorating training according to another embodiment of the inventive concept includes a controller and an input receiver, wherein the controller presents a virtual first object 10 on the screen, but the first object 10 is presented on the screen in an approaching manner from the first position to the second position. When the position of the first object 10 reaches the second position, the controller divides and presents the first object 10 on the screen or removes the first object 10 therefrom. After the first object 10 is divided and presented, or removed, the controller presents the virtual second object 20 and the visual third object 30 on the screen. The input receiving unit receives an identification input about the second object 20 and the third object 30 from the subject's response input device. The second position is closer to the subject than the first position is on the screen. The first position and the second position are located in the visual field center of the subject. The second object 20 and the third object 30 are positioned in at least one of the visual field center of the subject, the normal region of the subject visual field, and the defect region of the subject visual field.

The description of FIGS. 1 to 13 as described above is equally applied to the computing device for performing the visual field defect-ameliorating training of the inventive concept.

The steps of the method or the algorithm described in relation to the embodiments of the inventive concept may be directly implemented in hardware, implemented using a software module executed by the hardware, or implemented by a combination thereof. The software module may reside on Random Access Memory (RAM), Read Only Memory (ROM), Erasable Programmable ROM (EPROM), Electrically Erasable Programmable ROM (EEPROM), Flash Memory, hard disk, removable disk, CD-ROM, or a computer-readable recording medium of any form well known in the technical field to which the inventive concept belongs.

According to the inventive concept, presenting the stimulus in a flying manner may allow inducing the subject's concentration in the visual field defect-ameliorating training.

Further, according to the inventive concept, presenting various types of stimulus may allow presenting stimulus varying based on brain defect regions, thereby to achieve effective train the treatment.

Further, according to the inventive concept, presenting the stimulus while adjusting the shape of the stimulus, the movement speed of the stimulus, the angle thereof, the distance thereof, etc., may allow controlling the difficulty level based on the state of the subject, to achieve effective train the treatment.

Further, according to the inventive concept, presenting the stimulus three-dimensionally may allow the training to be implemented as a game, such that the subject's interest in the visual field defect-ameliorating training may be induced.

The effects of the inventive concept are not limited to the effects mentioned above. Other effects not mentioned will be clearly understood by those skilled in the art from the above description.

While the inventive concept has been described with reference to exemplary embodiments, it will be apparent to those skilled in the art that various changes and modifications may be made without departing from the spirit and scope of the inventive concept. Therefore, it should be understood that the above embodiments are not limiting, but illustrative.

What is claimed is:

1. A method for training a subject to ameliorate visual field defect of the subject based on a 3D (three-dimension) virtual reality using a head mounted display, the method comprising:
    outputting, by the head mounted display, a first object based on the 3D virtual reality on a screen of the head mounted display, wherein the first object is output in an approaching manner toward the subject from a first position to a second position;
    when a position of the first object reaches the second position, dividing, by the head mounted display, the first object into a plurality of first objects and outputting the divided first objects on the screen or removing, by the head mounted display, the first object from the screen;
    when the first object is divided or removed, outputting, by the head mounted display, a second object and a third object based on the 3D virtual reality on the screen; and
    receiving, by the head mounted display, an identification input about the second object and the third object from a response input device of the subject,
    wherein the first position and the second position are present in a central visual field of the subject, and
    wherein each of the second object and the third object is positioned in at least one of the central visual field of the subject, a normal region of a subject visual field, or a defect region of the subject visual field.

2. The method of claim 1, wherein the second object and the third object are output as a first combination, and
    wherein the first combination is configured such that one of the second object and the third object is positioned in the normal region of the subject visual field, while the other thereof is positioned in the defect region of the subject visual field.

3. The method of claim 2, wherein the second object and the third object are output as a predetermined ratio of the first combination and a second combination, and
    wherein the second combination is configured such that the second object and the third object are positioned in the normal region of the subject visual field.

4. The method of claim 1, wherein the second object and the third object are output as a third combination, and
    wherein the third combination is configured such that one of the second object and the third object is positioned at the central visual field of the subject, while the other thereof is positioned in the defect region of the subject visual field.

5. The method of claim 1, wherein when the first object is divided on the screen by the head mounted display, the first object is divided into a first sub object and a second sub object in the second position,
    wherein while the first object is divided, depths of the first sub object and the second sub object are adjusted to be the same as or different from that of the first object,
    wherein the outputting of the second object and the third object includes:
    outputting, by the head mounted display, the second object and the third object on a predetermined region of the screen instead of the first sub object and the second sub object, after the first object is divided into the first sub object and the second sub object.

6. The method of claim 1, wherein when the first object is removed from the screen by the head mounted display, the first object is removed from the screen in a scattered manner from the second position, in a spreading manner from the second position, or in the scattered manner or in the spreading manner from the second position, along with adjusting a depth at which the first object as being scattered or spread is present.

7. The method of claim 1, wherein the first object is output such that a color of the first object at the first position is different from a color of the first object at the second position,
    wherein the second object and the third object are output as a pattern corresponding to at least one of a horizontal pattern and a vertical pattern, and
    wherein the patterns of the second object and the third object are the same as or different from each other.

8. The method of claim 1, wherein the second object and the third object are output in the form of a rotating figure, and
    wherein a rotation directions of the second object and the third object are randomly output to be the same or different from each other.

9. The method of claim 1, wherein depths of the second object and the third object are randomly output to be the same or different from each other, and
    wherein the depths of the second object and the third object indicate a distance of the second object or the third object from the subject's eye position.

10. The method of claim 1, wherein at least one of a size, a position, an exposure time duration, and a contrast of the second object and the third object is changed based on a predetermined setting.

11. A head mounted display device for performing visual field defect-ameliorating training based on a 3D (three-dimension) virtual reality, the computing device comprising:
    a communication unit configured to communicate with a response input device of the subject;
    a display unit configured to output information related to the visual field defect-ameliorating training; and
    a processor configured to:
    output, on a screen of the display unit, a first object based on the 3D virtual reality, wherein the first object is output in an approaching manner toward the subject from a first position to a second position,
    when a position of the first object reaches the second position, divide the first object into a plurality of first objects,
    output the divided first objects on the screen or removing the first object from the screen,
    when the first object is divided or removed, output a second object and a third object based on the 3D virtual reality on the screen, and receive, via the communication unit, an identification input about the second object and the third object from the response input device of the subject,
wherein the first position and the second position are present in a central visual field of the subject, and
wherein each of the second object and the third object is positioned in at least one of the central visual field of the subject, a normal region of a subject visual field, or a defect region of the subject visual field.

12. The device of claim 11, wherein the second object and the third object are output as a first combination, and
wherein the first combination is configured such that one of the second object and the third object is positioned in the normal region of the subject visual field, while the other thereof is positioned in the defect region of the subject visual field.

13. The device of claim 12, wherein the second object and the third object are output as a predetermined ratio of the first combination and a second combination, and
wherein the second combination is configured such that the second object and the third object are positioned in the normal region of the subject visual field.

14. The device of claim 11, wherein the second object and the third object are output as a third combination, and
wherein the third combination is configured such that one of the second object and the third object is positioned at the central visual field of the subject, while the other thereof is positioned in the defect region of the subject visual field.

15. The device of claim 11, wherein when the first object is divided on the screen by the head mounted display, the first object is divided into a first sub object and a second sub object in the second position,
wherein while the first object is divided, depths of the first sub object and the second sub object are adjusted to be the same as or different from that of the first object,
wherein the processor is further configured to control the display unit to output the second object and the third object on a predetermined region of the screen instead of the first sub object and the second sub object, after the first object is divided into the first sub object and the second sub object.

16. The device of claim 11, wherein when the first object is removed from the screen, the first object is removed from the screen in a scattered manner from the second position, in a spreading manner from the second position, or in the scattered manner or in the spreading manner from the second position, along with adjusting a depth at which the first object as being scattered or spread is present.

17. The device of claim 11, wherein the first object is output such that a color of the first object at the first position is different from a color of the first object at the second position,
wherein the second object and the third object are output as a pattern corresponding to at least one of a horizontal pattern and a vertical pattern, and
wherein the patterns of the second object and the third object are the same as or different from each other.

18. The device of claim 11, wherein the second object and the third object are output in the form of a rotating figure, and
wherein a rotation directions of the second object and the third object are randomly output to be the same or different from each other.

19. The device of claim 11, wherein depths of the second object and the third object are randomly output to be the same or different from each other, and
wherein the depths of the second object and the third object indicate a distance of the second object or the third object from the subject's eye position.

20. The device of claim 11, wherein at least one of a size, a position, an exposure time duration, and a contrast of the second object and the third object is changed based on a predetermined setting.

* * * * *